(12) United States Patent
Woods

(10) Patent No.: US 7,951,171 B2
(45) Date of Patent: May 31, 2011

(54) POLYAXIAL SURGICAL ROD FIXATION ASSEMBLY

(75) Inventor: Richard W. Woods, Catonsville, MD (US)

(73) Assignee: K2M, Inc., Leesburg, VA (US)

( * ) Notice: Subject to any disclaimer, the term of this patent is extended or adjusted under 35 U.S.C. 154(b) by 516 days.

(21) Appl. No.: 11/417,130

(22) Filed: May 4, 2006

(65) Prior Publication Data

US 2007/0016192 A1 Jan. 18, 2007

(51) Int. Cl.
*A61B 17/70* (2006.01)

(52) U.S. Cl. ......... 606/264; 606/265; 606/266; 606/305

(58) Field of Classification Search ................... 606/264, 606/265, 266, 305
See application file for complete search history.

(56) References Cited

U.S. PATENT DOCUMENTS

| | | | |
|---|---|---|---|
| 5,443,467 A * | 8/1995 | Biedermann et al. | 606/65 |
| 5,733,286 A * | 3/1998 | Errico et al. | 606/266 |
| 6,113,601 A * | 9/2000 | Tatar | 606/266 |
| 6,595,993 B2 * | 7/2003 | Donno et al. | 606/71 |
| 6,835,196 B2 * | 12/2004 | Biedermann et al. | 606/308 |
| 6,893,444 B2 * | 5/2005 | Orbay | 606/281 |
| 7,141,051 B2 * | 11/2006 | Janowski et al. | 606/272 |
| 2002/0010467 A1 * | 1/2002 | Cooper et al. | 606/61 |
| 2002/0050190 A1 * | 5/2002 | Chandler et al. | 81/90.2 |
| 2003/0023240 A1 * | 1/2003 | Amrein et al. | 606/61 |
| 2005/0233281 A1 * | 10/2005 | Gittleman | 433/173 |

* cited by examiner

*Primary Examiner* — Eduardo C Robert
*Assistant Examiner* — David W Bates
(74) *Attorney, Agent, or Firm* — Carter, DeLuca, Farrell & Schmidt, LLP

(57) ABSTRACT

Provided is a surgical rod fixation assembly having a pedicle screw for insertion into spinal bone of a subject, the pedicle screw having a polyaxial mounted coupling member for driving the pedicle screw into bone on or off axis and coupling the pedicle screw to an orthopaedic device such as a spinal rod by means of a slidable coupling action.

23 Claims, 3 Drawing Sheets

POLYAXIAL SURGICAL ROD FIXATION ASSEMBLY

BACKGROUND OF THE INVENTION

1. Field of the Invention

The present invention relates to a surgical rod fixation assembly having a screw configured to provide a polyaxial rod coupling capability for use with orthopaedic fixation systems. More particularly, the present invention relates to a surgical rod fixation assembly having a pedicle screw for insertion into the spinal bone of a subject, the pedicle screw having a polyaxial mounted coupling member for coupling the pedicle screw to an orthopaedic device such as a surgical rod, or more particularly a spinal rod.

2. Background of the Technology

The fixation of surgical devices and appliances to bone is often difficult and time consuming, thus adding to the potential for trauma and complications in such surgical procedures. This is particularly true in spinal surgery procedures. Conventional locking mechanisms used to secure spinal rods to bone connectors such as pedicle screws have typically failed to provide the configurational versatility needed to make a secure attachment when individual bone configurations do not lend themselves to easy attachment.

Typically, conventional fixation systems, which attempt to provide the necessary versatility in quickly changing the configuration of the devices, employ too many small parts that serve only to complicate and prolong the surgical process and worse, can present hazards to the patient. Such conventional systems have attempted to avoid these problems but in doing so have had to sacrifice some of the configurational options that are needed for a best fit of the appliance.

Thus a need exists for a fixation assembly that can be easily and quickly used to provide the maximum flexibility in selecting a configuration for attachment of an appliance or surgical rod, such as a spinal rod, to the spine of a subject.

SUMMARY OF THE INVENTION

The present invention provides a novel polyaxial surgical rod fixation assembly having a surgical screw with a rotatable head securely held by an inner housing that is easily and slidably engaged with a complementary outer housing such that upon such engagement, the surgical screw is fixedly held in a relative position to the housing while the housing simultaneously securely holds the surgical rod.

Also provided is a method of using the assembly of the present invention such that minimal time and effort is required to set the assembly in the desired position relative to the anatomy of the subject.

Also provided is a kit that includes the assembly of the present invention in combination with at least one surgical rod to be placed in a subject.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF THE INVENTION

Detailed embodiments of the present invention are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

Figure 2A:
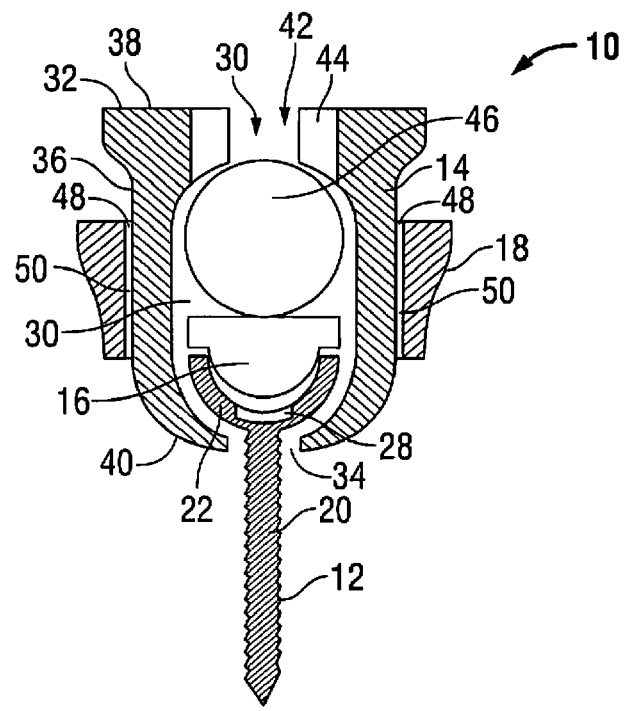
FIG. 2A is a cross sectional side view of the polyaxial surgical rod fixation assembly in an unlocked configuration.
Figure 2B:
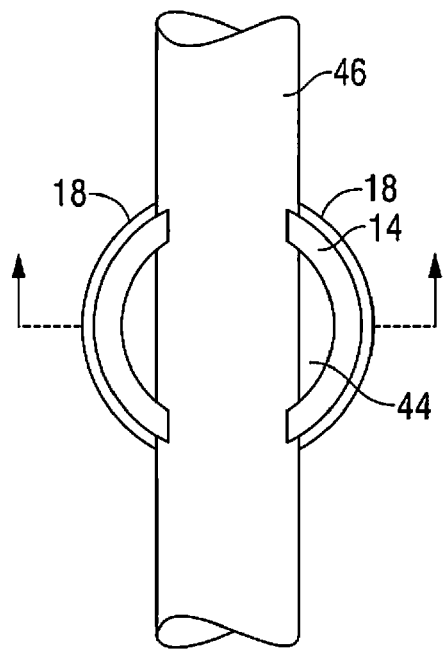
FIG. 2B is a top view of the polyaxial surgical rod fixation assembly shown in FIG. 2A.
Figure 2C:
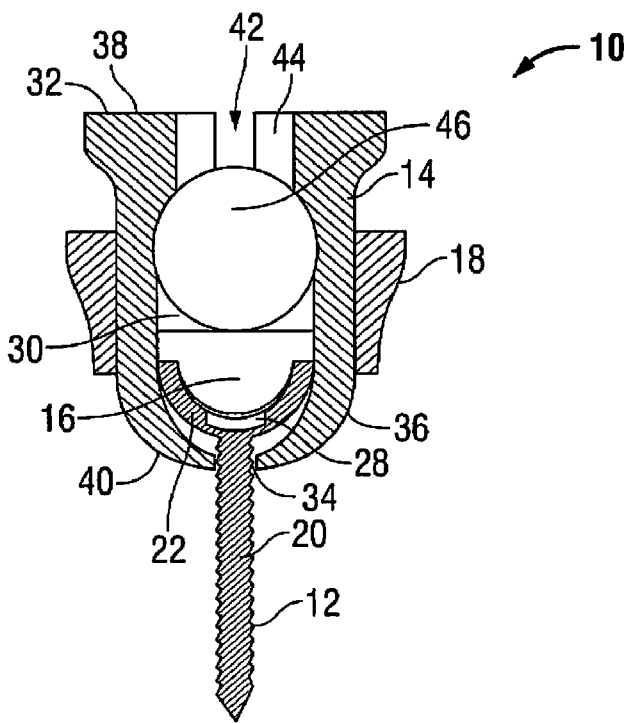
FIG. 2C is a cross sectional side view of the polyaxial surgical rod fixation assembly fully assembled in a locked configuration with a spinal rod securely held therein.
Figure 3A:
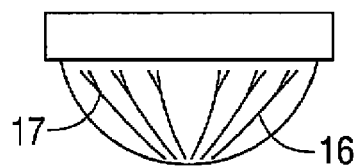
FIG. 3A provides a side view of a hemispherical insert member configured to be removably positioned within the polyaxial surgical rod fixation assembly shown in FIG. 2A.
Figure 3B:
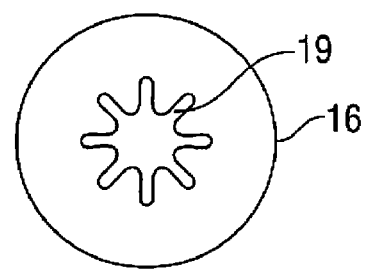
FIG. 3B is a top view of the hemispherical insert member shown in FIG. 3A, showing the drive receiving recess.

A novel polyaxial surgical rod fixation assembly, generally shown at 10, is illustrated in FIGS. 2A-2C. The assembly 10 of the present invention includes a screw member 12 configured to be inserted into and releasably retained within an inner housing 14 of the assembly 10. As best shown in FIGS. 3A-3B, a hemispherical insert 16 is provided to be positioned directly above and in engaging contact with the screw member 12, the insert 16 having position retention members 17 and drive supports 19 to facilitate positioning and retention of the insert within the inner housing 14. As best shown in FIGS. 2A-2C, an outer housing 18 is sized and configured to have an inner surface taper complementary to the outer lateral surface taper of the inner housing 14 and to be in slidable contact with and to circumscribe at least a portion of the outer lateral surface of the inner housing 14.

Figure 1A:
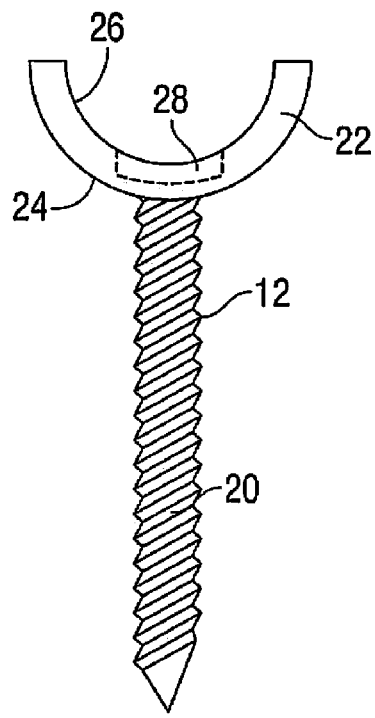
FIG. 1A provides a side view of the screw member of the present invention showing a bowl-shaped curvate head.
Figure 1B:
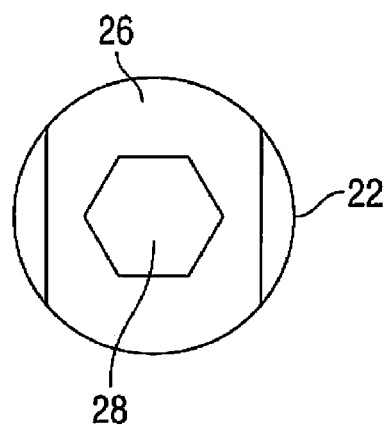
FIG. 1B is a top view of the screw member shown in FIG. 1A, the top view showing the spherical hexagonal configuration of the interior surface of the bowl-shaped curvate head.

As best shown in FIG. 1A-1B, the screw member 12 includes a threaded shaft 20, which is configured to penetrate and engage bone material so as to be removably fixed to the bone. The screw member 12 also includes a screw head 22 integrally formed with the screw shaft 20. As best shown in FIG. 1A, the screw head 22 is curvate in shape having a convex undersurface 24, preferably of a constant radius of curvature so as to be a section of a sphere. The screw head 22 has an interior surface 26, which is concave and also preferably of a constant radius of curvature so as to be capable of receiving the hemispherical insert 16. The interior surface 26 can have a configuration that can be complementary to the configuration of the corresponding contacting or under surface of the hemispherical insert 16. That is, the retention members 17 of the hemispherical insert 16 can be configured so as to interact with the configuration of the interior surface 26 of the screw head 22 such that a rotational movement of the hemispherical insert 16 will cause a similar rotational movement of the screw head 22. The retention members 17 of the insert 16 can preferably be configured as a hexagonal convex surface that conforms to a hexagonal concavity configuration of the interior surface 26 of the screw head 22. Other alternative configurations for the retention members such as, for example, square, triangular, octagonal, or raised-ribs or the like can be used so long as the configuration of the retention members on the under surface of the hemispherical insert 16 provide a gripping interaction with the configuration of the interior surface 26 of the screw head 22. As best shown in FIG. 1B, the interior surface 26 of the concavity of the screw head 22 can alternatively have an additional or secondary screw head concavity 28 defined in the lower portion of the interior surface 26 of the screw head 22. This alternative secondary concavity 28 can be configured in similar fashion to that described above for the interior surface 26 of the screw head 22. That is, the alternative secondary concavity can have a complementary configuration to a convex surface such as hexagonal, octagonal, square, ribbed or the like so long as the interaction between the secondary concavity 28 and the under surface of the hemispherical insert 16 results in sufficient gripping action to allow transfer of rotational motion of the hemispherical insert 16 to rotational motion of the screw head 22.

As best shown in FIGS. 3A-3B and discussed above, the hemispherical insert 16 has a convex undersurface with position retention members 17, which contact the gripping interior surface 26 or alternative the secondary concavity 28 This gripping interaction between the hemispherical insert 16 and the interior surface 26 of the screw member 12 allows a tightening or loosening tool to be inserted into contact with the drive support 19 of the hemispherical insert 16 with good effect even when the longitudinal axis of the screw member 12 is not aligned with the longitudinal axis of the hemispherical insert 16. Thus, screw member 12 tightening or loosening can be accomplished off-axis providing a significant improvement in flexibility for the surgeon. In operation, the gripping action of the retention members 17 of hemispherical insert 16 with the complementary configured interior surface 26 or secondary concavity 28 of the screw head 22 serves to transfer the rotational motion from the hemispherical insert 16 to the screw member 12. Thus, when a tightening or loosening tool is inserted into contact with drive support 19 of the hemispherical insert 16 and rotational forces are applied by an operator the rotational force is transferred to the screw head 22. This transfer of rotational motion from the insert 16 to the screw head 22 by the interaction of the retention members 17 permits the screw member 12 to be rotated to a tightened or loosened position without regard for whether the axis of the insert 16 is in alignment with the axis of the screw member 12. By this mechanism, the polyaxial tightening or loosening capacity of the invention is realized. While the preferred configuration of the retention members 17 on the under surface of the insert 16 is of a hexagonal convex shape and the interior surface 26 of the screw head 22 has the shape of a hexagonal concavity, the particular configurations of the interacting surfaces can be quite varied as indicated above without departing from the concept of the invention.

The inner housing 14, into which the screw member 12 can be inserted, defines an axial bore 30, which extends from the upper surface 32 along the longitudinal axis of the inner housing 14 to a screw shaft exit portal 34, which is sized and configured to permit the threaded shaft 20 of the screw member 12 to extend below and outside of the inner housing 14 but is also sized so as to not permit the screw head 22 to pass through the exit portal 34. The outer surface 36 of the inner housing 14 is provided with a taper between an inner housing first end 38 and an inner housing second end 40, the diameter of the inner housing 14 decreasing from the inner housing first end 38 to the inner housing second end 40. The inner housing from first end 38 to second end 40 defines an inner housing slit 42, which is sized to permit limited inward compression of the inner housing when an external force is applied to the outer surface 36 of the inner housing 14. The inner housing 14 proximate to the first end 38 defines a surgical rod receiving portal 44, which is sized and configured to moveably receive a surgical rod 46. While it is preferable that the surgical rod receiving portal 44 does not extend so far toward the first end 38 of the inner housing 14 so as to open out beyond the upper limit of the inner housing; that is to form a slot instead of a portal, it is still within the concept of the invention that a surgical rod could be placed and securely held in such a slot by the present invention.

The outer housing 18 of the assembly 10 defines an inner passageway 48, which is sized and configured with an inner surface 50 having a taper that is complementary to that of the outer surface 36 of the inner housing 14. The inner passageway 48 of the outer housing 18 is sized and tapered so as to slidably fit circumferentially about the outer surface 36 of the inner housing 14 in such a manner so as to exert a compressing force against the outer surface 36 of the inner housing 14 when the outer housing 18 is fully in place around the circumference of the inner housing 14.

In operation, as the inner housing 14 and the outer housing 18 are slidably joined along their coincidental longitudinal axis and contacting the complementary tapered outer surface 36 and inner surface 50 limited inward compression of the inner housing 14 results. This inward compression of the inner housing 14 is sufficient to force the axial bore 30 of the inner housing 14 into a locking compressive engagement against the surgical rod 46, which is resident in the surgical rod receiving portal 44. Further, compression of the inner housing 14, as caused by the circumferential engagement of the outer housing 18 with the inner housing 14 causes sufficient compression to force the axial bore 30 of the inner housing 14 into a locking compressive engagement against the screw head 22 thus securely holding the screw member 12 in a fixed position relative to the inner housing 14 when an external force is applied to the outer surface 36 of the inner housing 14. Alternatively, the inner housing 14 and the outer housing 18 can be configured such that when the outer housing 18 is moved into a locking position in relation to the inner housing 14, the compression of the inner housing 14 is sufficient to lock a surgical rod 46 into a fixed position relative to the inner housing 14 but does not enter into a compressive engagement against the screw head 22; thus, leaving the screw head 22 free to move relative to the inner housing 14.

Thus, the present invention provides a polyaxial surgical rod fixation assembly that enables a user to securely but releasably connect a surgical rod to bone with a device having fewer parts and greater simplicity of use than that conventionally provided.

It is within the concept of the present invention to provide the polyaxial surgical rod fixation assembly described above in a kit including at least one surgical rod that can be positioned and secured within a subject in need thereof. Such a kit can be provided in sterile packaging for opening and immediate use in the operating room.

The components of the present invention can be manufactured using methods and materials as known in the art such as for example, implant grade metallic materials, such as titanium, cobalt chromium alloys, stainless steel, and the like. It is also within the concept of the present invention that the components can be manufactured from any bio-compatible materials such as composite materials or plastics. Non-limiting examples of such materials include polyetheretherketone (PEEK) or polyaryletherketone (PAEK), or composites thereof, which can incorporate carbon fibers or similar materials. The materials used in the manufacture of the device and components of a kit can be radiopaque or radiolucent. The components of the present invention can be manufactured by any of a variety of known methods to include, for example, molding, casting, forming, machining, and extruding.

The method of the present invention provides for the implantation of the system of the present invention in a subject in need of the same. Variations of standard method steps in such surgical procedures can be made to adapt to the specific needs of the subject without departing from the concept of the invention. Normal operative techniques and tools for implantation of the device can be employed as necessary in accordance with safe surgical practices. A particular convenience of the present invention is the ease by which the device with a surgical or spinal rod in place can be releasably locked by simply sliding the outer housing 18 upward along the outer surface of the inner housing. By this method the slit of the inner housing is compressed together so as to decrease the size of the upper portion of the axial bore 30 of the inner housing thus holding the surgical or spinal rod in place.

Each of the embodiments described above are provided for illustrative purposes only and it is within the concept of the present invention to include modifications and varying configurations without departing from the scope of the invention that is limited only by the claims included herewith. While the descriptive example of the present invention is primarily directed to securing of a spinal rod, it is within the concept of the present invention to employ assembly to releasably secure any surgical rod in place.

Each of the embodiments described above are provided for illustrative purposes only and it is within the concept of the present invention to include modifications and varying configurations without departing from the scope of the invention that is limited only by the claims included herewith.

What is claimed is:

1. A surgical rod fixation assembly, comprising:
   a surgical screw, having a screw head and a threaded shaft,
   an inner housing having a tapered outer surface and configured to hold the screw head within the inner housing while permitting the screw shaft to extend outside of the inner housing, the inner housing also being configured to releasably hold a portion of a surgical rod, the wall of said inner housing having a compressible slit,
   a force transfer element having an under surface and an upper surface and being sized and configured to fit within said inner housing, said force transfer element being positioned above said screw head with said under surface being in direct gripping contact with said screw head and said upper surface defining drive supports configured to interact with a tool, said force transfer element being capable of on and off axis translation of rotational motion to said screw head operative to tighten or loosen the screw into bone, and
   an outer housing having a tapered inner surface complementary to the taper of said inner housing, said outer housing being sized and configured to be circumferentially and slidably positioned around the inner housing,
   wherein the size of said compressible slit is capable of being decreased by a compressing force exerted as said outer housing is slidably positioned along the longitudinal axis of said inner housing so as to securely hold at least said surgical rod in a releasably locked position relative to said inner housing.

2. The assembly of claim 1, wherein said surgical rod is a spinal rod and said assembly is capable of compressing said inner housing so as to hold said spinal rod and said screw in releasably locked position relative to said inner housing when said outer housing is slidably positioned along the longitudinal axis of said inner housing.

3. The assembly of claim 2, wherein said screw head presents an interior surface and an exterior curvate surface, said exterior curvate surface being configured so as to be capable of movement within said inner housing.

4. The assembly of claim 3, wherein said interior surface of said screw head is configured to provide a gripping surface to facilitate tightening or loosening rotational movement of the screw head when engaged with said force transfer element, said force transfer element comprising retention members on said under surface to facilitate gripping contact with said interior surface of said screw head.

5. The assembly of claim 4, wherein said interior surface of said screw head has a concave configuration, said configuration being selected from the group consisting of a hexagon, a square, a rectangle, a triangle, a multi-pointed star, a ribbed or grooved hemisphere, and an oval.

6. The assembly of claim 5, wherein said retention members are configured to be complementary to said concave configuration of said interior surface of said screw head,
   whereby tightening or loosening rotational forces applied to said upper surface drive supports can be transferred via said under surface retention members to said gripping interior surface of said screw head to effect rotational forces to said surgical screw.

7. The assembly of claim 6, wherein said retention members of said hemispherical insert has a configuration selected from the group consisting of a convex surface shaped as a hexagon, a square, a rectangle, a triangle, a multi-pointed star, a ribbed or grooved hemisphere, and an oval.

8. The assembly of claim 7, wherein said interior surface of said screw head is a hexagonal concavity and said retention members of said under surface of said hemispherical insert have a complementary convex-shaped configuration to that of said hexagonal concavity.

9. The assembly of claim 3, wherein said interior surface defines a secondary concavity within said screw head, said secondary concavity having a complementary configuration to the configuration of said retention members of said hemispherical insert such that any rotational movement of said hemispherical insert can be transferred to rotational movement of said screw head.

10. The assembly of claim 9, wherein said complementary configuration of said secondary concavity has a configuration selected from the group consisting of a hexagon, a square, a rectangle, a triangle, a multi-pointed star, a ribbed or grooved hemisphere, and an oval.

11. The assembly of claim 2, wherein said inner housing comprises a screw shaft exit portal that is sized and configured to permit the threaded shaft of said screw to extend below and outside of said inner housing while retaining the screw head of said screw within said inner housing.

12. The assembly of claim 10, wherein said drive supports of said hemispherical insert have a complementary configuration to the gripping surface of a tightening or loosening tool.

13. The assembly of claim 2, wherein said assembly is manufactured of materials comprising material selected from the group consisting of implant grade metallic material, titanium, cobalt chromium alloys, stainless steel, bio-compatible composite materials, plastics, and combinations thereof.

14. The assembly of claim 13, wherein said material are radiopaque or radiolucent.

15. The assembly of claim 13, wherein said assembly is manufactured by a method selected from the group consisting of molding, casting, forming, machining, extruding, and combinations thereof.

16. A kit for connecting a surgical rod to bone, said kit comprising:
- at one surgical rod fixation assembly according to claim 1 and
- at least one surgical rod.

17. The kit according to claim 16, wherein said at least one surgical rod fixation assembly is two or more assemblies.

18. The kit according to claim 17, wherein said two or more assemblies comprise screws of different sizes.

19. A surgical rod fixation assembly, comprising:
- a surgical screw having a screw head and a threaded shaft, the screw head including a gripping surface defined on an interior surface thereof;
- an inner housing having a tapered outer surface, the surgical screw configured such that the screw head is disposed in the inner housing while the screw shaft extends distally from the inner housing, the inner housing configured to releasably retain a portion of a surgical rod therein, a wall of the inner housing having a compressible slit defined therethrough;
- a force transfer element dimensioned and configured for positioning within the inner housing adjacent to and proximal of the screw head, the force transfer element having an upper surface and a lower surface, the lower surface of the force transfer element being engageable with the gripping surface of the screw head such that both on and off axis rotation of the force transfer element effects corresponding rotational motion of the screw head operative to tighten or loosen the screw into bone; and
- an outer housing having a tapered inner surface complementary to the taper of the inner housing, the outer housing being dimensioned and configured to be circumferentially and slidably positioned around the inner housing;
- wherein the compressible slit is compressed as the outer housing is translated proximally with respect to the inner housing along the longitudinal axis thereof such that the surgical rod is retained in a releasably locked position relative to the inner housing.

20. The assembly of claim 19, wherein the force transfer element includes retention members disposed on the lower surface thereof to facilitate corresponding rotational motion of the screw head upon rotation of the force transfer element when the screw head and the force transfer element are engaged with one another.

21. The assembly of claim 19, wherein the compression of the compressible slit locks the screw head in a releasably locked position relative to said inner housing.

22. The assembly of claim 1, wherein off axis translation of rotational motion is defined when a longitudinal axis of the force transfer element and a longitudinal axis of the threaded shaft define an acute angle therebetween.

23. The assembly of claim 19, wherein off axis translation of rotational motion is defined when a longitudinal axis of the force transfer element and a longitudinal axis of the threaded shaft define an acute angle therebetween.

* * * * *